United States Patent
Mozzi et al.

(10) Patent No.: US 8,321,027 B2
(45) Date of Patent: Nov. 27, 2012

(54) TRANSCUTANEOUS POWER SUPPLY WITH OPTIMAL POSITIONING FOR USE WITH ACTIVE IMPLANTABLE DEVICES

(75) Inventors: Aldo Mozzi, Padua (IT); Eugenio Snichelotto, Padua (IT)

(73) Assignee: Medico S.p.A., Padua (IT)

( * ) Notice: Subject to any disclaimer, the term of this patent is extended or adjusted under 35 U.S.C. 154(b) by 775 days.

(21) Appl. No.: 11/752,278

(22) Filed: May 22, 2007

(65) Prior Publication Data

US 2007/0279020 A1    Dec. 6, 2007

(30) Foreign Application Priority Data

May 19, 2006   (IT) ................................. PD2006A0198
May 22, 2006   (EP) ..................................... 06425341

(51) Int. Cl.
*A61N 1/00*   (2006.01)

(52) U.S. Cl. ................................ 607/60; 607/61; 607/65
(58) Field of Classification Search .............. 607/60–61, 607/65
See application file for complete search history.

(56) References Cited

U.S. PATENT DOCUMENTS 6,473,652 B1 * 10/2002 Sarwal et al. ................... 607/62
2005/0267549 A1 * 12/2005 Della Santina et al. ......... 607/57

* cited by examiner

*Primary Examiner* — Nicole F Lavert
(74) *Attorney, Agent, or Firm* — Themis Law

(57) ABSTRACT

The transcutaneous power supply and/or recharger device of the present invention enables a precise centering of the device with a receiver coil in an implant. In one embodiment, the power supply device includes a plurality of satellite sensors or coils disposed around the transmitter coil. A voltage value detected in the receiver coil is transmitted to the power supply or recharger device via a telemetric channel and indicates the amount of power being transferred, and, therefore, the accuracy of the reciprocal positioning of the power supply terminal with the receiver coil.

15 Claims, 1 Drawing Sheet

TRANSCUTANEOUS POWER SUPPLY WITH OPTIMAL POSITIONING FOR USE WITH ACTIVE IMPLANTABLE DEVICES

FIELD OF THE INVENTION

The present invention relates to implantable medical devices. More particularly, the present invention relates to transcutaneous electrical power supply and/or recharging systems for implantable medical devices.

BACKGROUND OF THE INVENTION

In some electronic systems implanted in the human body, power must be supplied from an outside device to the implanted device (or implant).

Said power supply is normally provided by inductively coupling a coil, called the transmitter and located outside the patient's body, to a coil called the receiver, which is implanted just below the patient's skin and is either connected to or incorporated into the implant.

The transmitter coil generates a field that is picked up and converted into electric current by the receiver coil when it is aligned with said transmitter coil.

The energy transferred to the implant can be exploited immediately or stored in a rechargeable battery for later use.

The outside device is hereinafter called the power supply, although it may equally operate as a battery recharger.

The effectiveness of the power transfer between the two coils is rather sensitive and depends mainly on the reciprocal positioning, i.e. on the coupling between the two coils.

The best performance is obtained when the two coils, the transmitter and the receiver, are perfectly aligned, but this alignment is not easy to achieve because the exact position of the receiver coil is difficult to identify.

Any displacement or misalignment between the two coils reduces the efficiency of the energy transfer, with a smaller quantity of energy consequently being transferred to the implant, and/or increases the time needed to recharge the implant's battery.

Moreover, a part of the energy delivered by the transmitter coil that is not transferred to the receiver coil is absorbed by the tissues surrounding the coils, giving rise to an increase in the temperature of said tissues.

Given the time required for the transmitter coil to recharge the implant's battery or to power the implant, exposing the tissues to the energy that is not absorbed by the receiver coil can have side effects of various types, ranging from mere discomfort to lesions with severe consequences.

Other known electronic implantable devices include a telemetric intercommunication system that enables the transfer of information from the implant to other, outside devices, such as a programmer, a function monitor, a power supply, a recharger, and so on. Such telemetric systems are used to record and to set the implant's working parameters, to record historical data on how the implant functions, and to receive and transmit other similar information.

BRIEF SUMMARY OF THE INVENTION

The present invention relates to a transcutaneous power supply and/or recharger for use with implants that enables a precise positioning and centering over the receiver coil and thereby facilitates a better alignment between the transmitter coil and the receiver coil.

An aspect of the power supply and/or recharger device of the present invention is to improve the positioning of the transmitter coil of the power supply device in relation to the receiver coil of the device implanted in the patient's body by providing a quantitative indication of the power transfer being received at any given time.

Another aspect of the power supply and/or recharger device of the present invention is to facilitate the precise positioning of the transmitter coil of the power supply device in relation to the receiver coil of the device implanted in the patient's body by providing an indication to the operator of the direction in which the transmitter coil on the outside needs to be moved in order to be positioned precisely over the receiver coil.

Another aspect of the power supply and/or recharger device of the present invention is to facilitate the positioning of the transmitter coil of the power supply device in relation to the receiver coil of the device implanted in the patient's body without requiring guide marks or reference points on the patient's body.

These and other, direct and complementary aspects are achieved through the implementation of a transcutaneous power supply and/or recharger device for implants that enables a precise and centered positioning over the receiver coil of the implant, wherein the quantity of current received by the receiver coil is monitored by the implant, and wherein the power supply terminal of the power supply device is fitted with satellite sensors or coils arranged around the transmitter coil.

The recorded receiver coil voltage value may be sent to the power supply or recharger device via the existing telemetric channel, and may indicate the quantity of power transfer underway, thereby identifying the degree of precision of the positioning between the power supply terminal and the receiver coil.

The power supply terminal's satellite coils or sensors (of which there are at least three, arranged around the transmitter coil) pick up signals and/or fields that depend on the transmitter coil and on the metal bodies in the immediate vicinity.

At rest, the satellite sensors or coils pick up a signal and/or field caused by the transmitter alone. When the transmitter coil is positioned perfectly over the receiver coil, the power supply terminal's satellite coils or sensors receive a different, weaker signal and/or field due to the presence of the receiver coil.

If the transmitter coil is not positioned perfectly over the receiver coil, however, the satellite coils or sensors receive a signal and/or field that is different from the signal received from the transmitter coil alone, which depends on their distance from the receiver coil. Said difference in signal and/or field is recorded and used to provide a visual indication to the operator about the direction to which to move the power supply terminal and the corresponding transmitter coil, in order to position it perfectly over the receiver coil.

The characteristics of the new transcutaneous power supply and/or recharger device for implants that provides a precisely centered positioning over the receiver coil of the implant will be better explained in the following description with reference to the attached drawings, which illustrate a non-limiting embodiment.

BRIEF DESCRIPTION OF THE SEVERAL VIEWS OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

FIGS. 1a and 1b illustrate an outer view and inner view, respectively, of an embodiment of the power supply terminal.

DETAIL DESCRIPTION OF EMBODIMENTS OF THE INVENTION

Figure 1B:
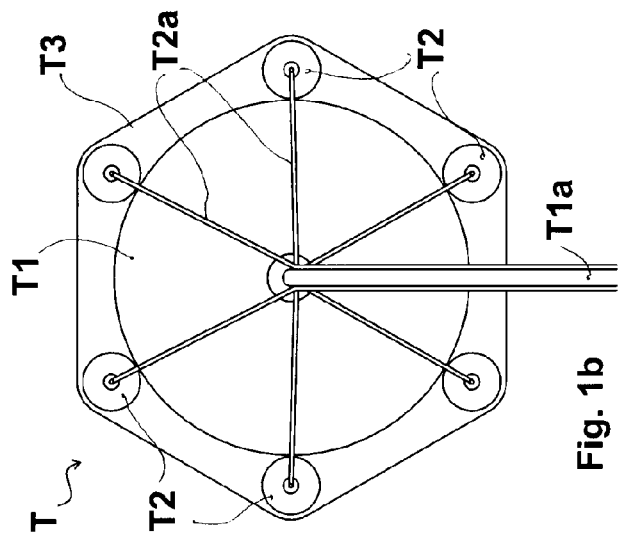
Figure 1A:
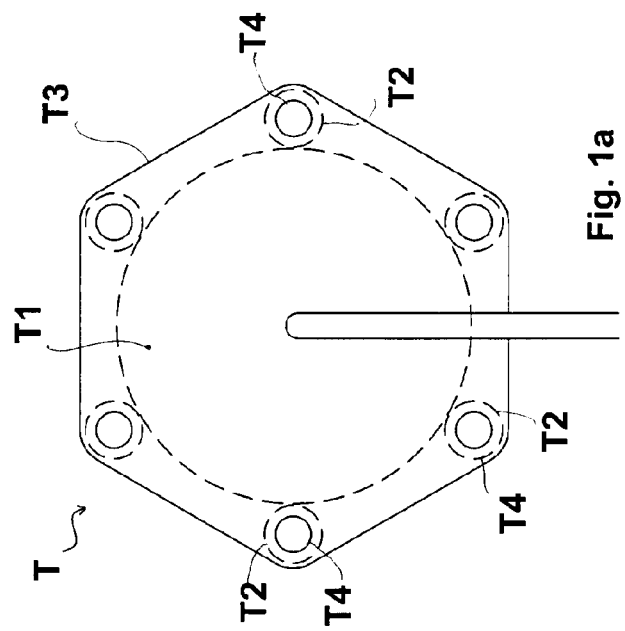

FIGS. 1a and 1b show an outer view and inner view, respectively, of an embodiment of a power supply terminal (T) according to an embodiment of the invention that includes a holder (T3) containing a transmitter coil (T1) suitable for generating a power transmission field, and a number of smaller satellite coils or sensors (T2) arranged around said transmitter coil (T1).

The satellite coils or sensors (T2) may consist of small coils, possibly provided with a ferromagnetic core, or other types of sensors, e.g. Hall sensors.

In the present embodiment, for ease of description, reference is made to satellite coils (T2) consisting of coils with a ferromagnetic core.

The satellite coils (T2) lie on the same plane as the transmitter coil (T1).

These satellite coils (T2) can be arranged in any manner around the transmitter coil (T1), but are preferably placed equidistant from one another and also equidistant from the center of said transmitter coil (T1), i.e. in line with the vertices of a regular polygon concentric with the transmitter coil (T1).

One or more indicators (T4) are provided on the holder (T3) of the power supply terminal (T).

These indicators (T4) may consist, for instance, of a single display in a central position, or of various displays coinciding with the satellite coils (T2), or luminous indicators arranged in line with the satellite coils (T2), or analog indicators with dials placed in line with the satellite coils (T2).

The transmitter coil (T1) is connected to the power supply device (not shown) by means of a corresponding cable (T1a).

Each satellite coil (T2) is connected to a measurement and control circuit of the power supply device by means of a suitable cable (T2a).

Each satellite coil (T2) picks up a signal and/or field that depends on the transmitter coil (T1) and on any metal bodies in the vicinity.

At rest, the satellite coils (T2) perceive a signal and/or field that is due to the transmitter coil alone (T1). In this situation, the circuit controlling the power supply device can perform a calibration to determine the neutral position and the baseline reception of the satellite coils (T2), and can consequently represent a baseline or reference value or information on the various indicators (T4) distributed in line with the various satellite coils (T2), or can represent a centering signal on a single central indicator.

If the satellite coils (T2) are equidistant from one another and from the transmitter coil (T1), then all the satellite coils (T2) receive the same signal and/or field and all the indicators (T4) consequently provide the same indication.

Figure 2B:
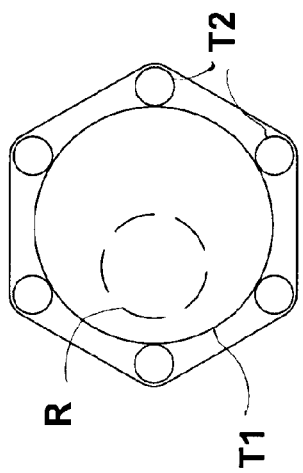
FIGS. 2a and 2b illustrate the power supply terminal of FIG. 1a positioned in relation to a receiver coil, and, more particularly, in a centered position FIG. 2a, and in an off-center position in FIG. 2b.
Figure 2A:
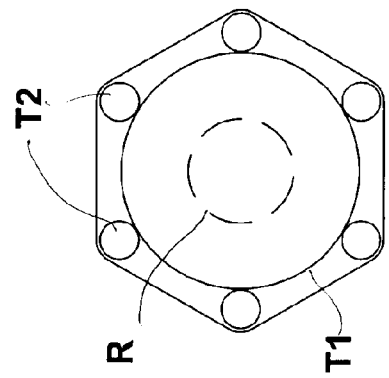

When the transmitter terminal (T), and the transmitter coil (T1) in particular, are perfectly centered over the receiver coil (R), as illustrated in FIG. 2a, the satellite coils (T2) of the power supply terminal (T) all receive the same signal and/or field, which differs from the signal and/or field perceived in the presence of the transmitter coil (T1) alone.

Once the geometry of a given application has been defined, the flows in the satellite coils (T2) as a function of the position of the receiver coil (R) can be mapped and used for a more straightforward and/or precise calculation of the direction, or to eliminate the power supply calibration stage.

If the power supply terminal (T), and the transmitter coil (T1) in particular, are not positioned exactly over the receiver coil (R), as shown for example in FIG. 2b, the satellite coils (T2) receive a different signal and/or field, which depends on their distance from the receiver coil (R), which differs from the signal and/or field received in the presence of the transmitter coil alone (T1). Said difference in signal and/or field is recorded and compared by a control circuit coupled to the power supply device and is used to provide a visual indication for the operator, by means of the indicators (T4), about the direction to which to move the power supply terminal (T) in order to position the transmitter coil (T1) exactly over the receiver coil (R).

By measuring the difference between the calibrated flow and the flow actually received, a microprocessor incorporated in the power supply device can identify which of the satellite coils (T2) is nearest to the receiver coil (R) and thus indicate the direction to which to move the power supply terminal (T), in order to center the power supply terminal over the receiver coil (R). Using simple vector calculation methods, intermediate directions between two satellite coils (T2) can also be calculated.

The receiver coil (R) and implant containing the receiver coil continuously monitor the measurement of the voltage at the terminals of the receiver coil (R).

The voltage value recorded in the receiver coil (R) is sent by the implant to the power supply or recharger via a telemetric channel, indicating the quantity of the power transfer underway and thus the accuracy of the positioning of the power supply terminal (T) and receiver coil (R).

The new transcutaneous power supply and/or recharger device for implants configured for an accurately centered positioning over the receiver coil provides a precise positioning of the power supply terminal (T), or transmitter coil (T1), over the receiver coil (R) of the device implanted in a patient's body.

More particularly, the power supply and/or recharger device described above provides a more accurate positioning of the transmitter coil (T1) over the receiver coil (R) of a device implanted in a patient's body by providing the operator with an indication of the direction in which the power supply terminal (T), and thus the transmitter coil (T1), needs to be moved in order to obtain the perfect alignment between the transmitter coil (T1) and the receiver coil (T2). One skilled in the art will appreciate that the above described power supply and/or recharger device may be configured for manual or automatic positioning in relation to the receiver coil (R).

The new power supply and/or recharger device as described above also enables a constant monitoring of the efficiency of the power transfer from the transmitter coil (T1) to the receiver coil (R).

The present description provides a person skilled in the art with sufficient information to implement the invention, but variants may be introduced that are all included within the scope and spirit of the present invention.

Thus, with reference to the previous description and to the attached drawings, the following claims are put forth.

What is claimed is:

1. A transcutaneous power supply for an implant having a receiver coil, the transcutaneous power supply comprising:
   a transmitter coil external to a body;

three or more satellite sensors situated peripherally in relation to of the transmitter coil, the satellite sensors being adapted to receive a signal generated by the transmitter coil, the satellite sensors being further adapted to detect a change in the signal caused by a changing position of the transmitter coil in relation the receiver coil;

a control circuit electrically connected to the satellite sensors, the control circuit measuring the signal and comparing the signal to a baseline value; and three or more indicators electrically connected to the control circuit;

a housing containing the transmitter coil, the satellite sensors, and the indicators, wherein the control circuit causes changes in the indicators according to the change in the signal such to cause a visual indication of a direction to move the power supply to position the transmitter coil over the receiver coil for optimal power transmission.

2. The transcutaneous power supply of claim 1, wherein the transcutaneous power supply is a recharger for the implant.

3. The transcutaneous power supply of claim 1, wherein the sensors are positioned on an outer surface of the housing.

4. The transcutaneous power supply of claim 3, wherein the indicators are in equal number to the sensors, the indicators being arranged in coincident positions with the sensors.

5. The transcutaneous power supply of claim 1, wherein the visual indication is provided by a luminous indicator or a visual display.

6. The transcutaneous power supply of claim 1, wherein the satellite sensors comprise one or more electric coils.

7. The transcutaneous power supply of claim 6, wherein the one or more electric coils each have a ferro-magnetic core.

8. The transcutaneous power supply of claim 1, wherein the signal comprises a magnetic field.

9. The transcutaneous power supply of claim 1, wherein the satellite sensors are equidistant one from the other.

10. The transcutaneous power supply of claim 1, wherein the satellite sensors are equidistant from a center of the transmitter coil.

11. The transcutaneous power supply of claim 10, wherein the satellite sensors are positioned in a polygonal pattern.

12. The transcutaneous power supply of claim 1, wherein the transmitter coil and the satellite sensors are coplanar.

13. The transcutaneous power supply of claim 1, further comprising a microprocessor processing the signal such to determine the changes in the indicators.

14. The transcutaneous power supply of claim 1, wherein at least one of the indicators comprises a display.

15. The transcutaneous power supply of claim 1, wherein the satellite sensors are adapted to telemetrically receive from the implant a measurement of a voltage at terminals of the receiver coil.

* * * * *